United States Patent
Kim et al.

(10) Patent No.: US 7,655,284 B2
(45) Date of Patent: Feb. 2, 2010

(54) MULTI-FUNCTIONAL MONOMER HAVING A PHOTOREACTIVE GROUP, ALIGNMENT FILM FOR LCD USING THE MONOMER, AND LCD COMPRISING THE ALIGNMENT FILM

(75) Inventors: Kyung Jun Kim, Daejeon Metropolitan (KR); Keon Woo Lee, Daejeon Metropolitan (KR); Byung Hyun Lee, Daejeon Metropolitan (KR); Min Young Lim, Sungnam-si (KR); Hye Won Jeong, Daejeon Metropolitan (KR); Jung Ho Jo, Anyang-si (KR); Heon Kim, Daejeon Metropolitan (KR); Sung Joon Oh, Daejeon Metropolitan (KR); Sung Ho Chun, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 307 days.

(21) Appl. No.: 11/525,056

(22) Filed: Sep. 22, 2006

(65) Prior Publication Data

US 2007/0098922 A1 May 3, 2007

(30) Foreign Application Priority Data

Sep. 22, 2005 (KR) ............... 10-2005-0088317

(51) Int. Cl.
*C08F 265/04* (2006.01)
*C08F 267/06* (2006.01)
*C09K 19/56* (2006.01)

(52) U.S. Cl. ............... 428/1.33; 428/1.2; 252/299.66; 252/299.67; 427/520; 427/521; 427/163.1; 349/124; 525/304

(58) Field of Classification Search ............... 428/1.2, 428/1.33; 252/299.01, 299.66–299.67; 525/302, 525/304; 526/321; 427/163.1, 372.2, 487, 427/520–521; 349/123–136
See application file for complete search history.

(56) References Cited

U.S. PATENT DOCUMENTS

| 5,998,101 A | 12/1999 | Park et al. |
| 6,833,391 B1 * | 12/2004 | Chisholm et al. ............... 522/28 |
| 7,070,838 B2 * | 7/2006 | Sasada et al. ............... 428/1.1 |

FOREIGN PATENT DOCUMENTS

| JP | 11-181127 | 7/1999 |
| JP | 2004-188679 | 7/2004 |
| WO | WO 2004/002935 A1 | 1/2004 |

OTHER PUBLICATIONS

Jeoung-Yeon Hwang et al., "Liquid Crystal Alignment and Pretilt Angle Generation on a Photopolymer Layer Based on N-(phenyl)maleimide," Liquid Crystals, 2002, vol. 29, No. 8, pp. 1047-1050.

* cited by examiner

*Primary Examiner*—David R Sample
*Assistant Examiner*—Sophie Hon
(74) *Attorney, Agent, or Firm*—McKenna Long & Aldridge LLP

(57) ABSTRACT

Disclosed is a multi-functional monomer including a heat-curable functional group as well as a typical photoreactive group. In the multi-functional monomer, the photoreactive group is not chained to a main chain of a polymer. Thus, since it is possible to perform desirable alignment treatment even though polarized UV is radiated for a short time, the production time and the production cost are reduced and alignment regulating force of liquid crystals is increased, thereby increasing a dichroic ratio.

16 Claims, 9 Drawing Sheets

[Fig. 1]
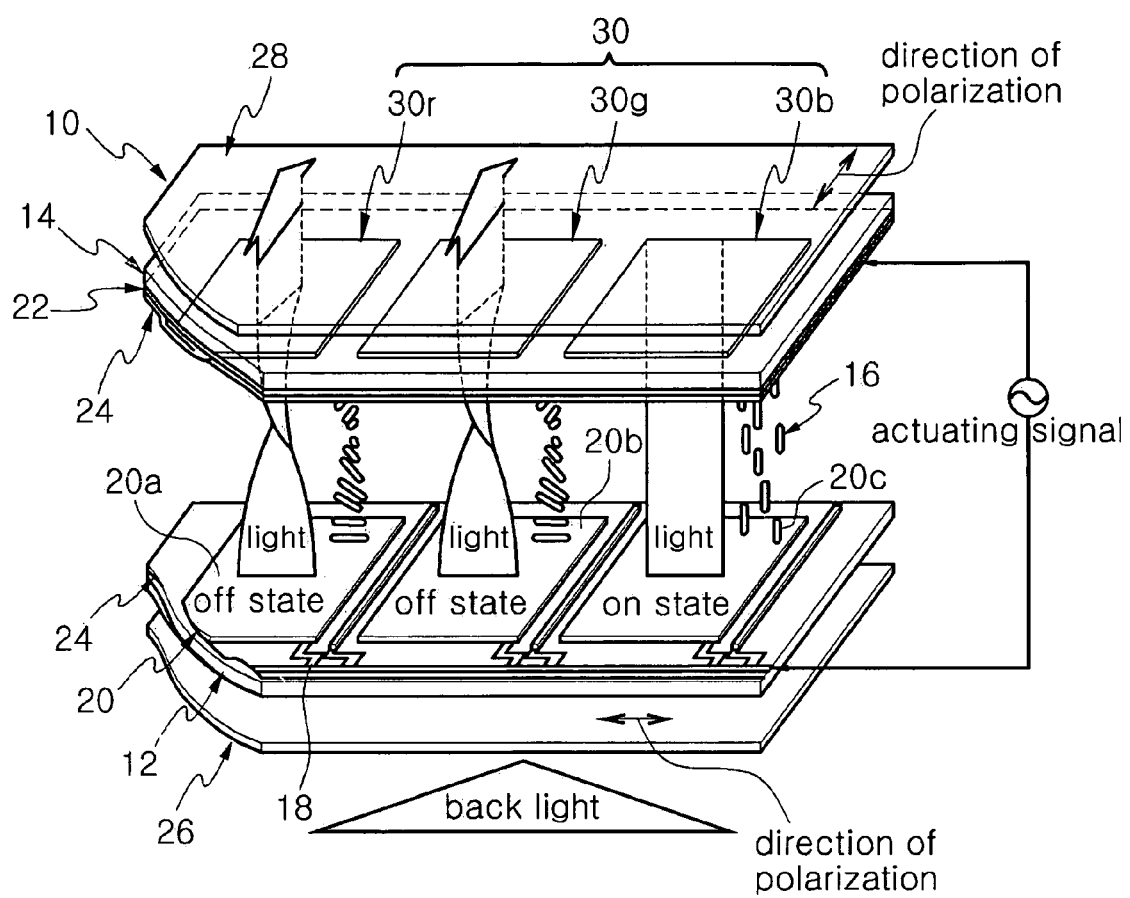

[FIG. 2]
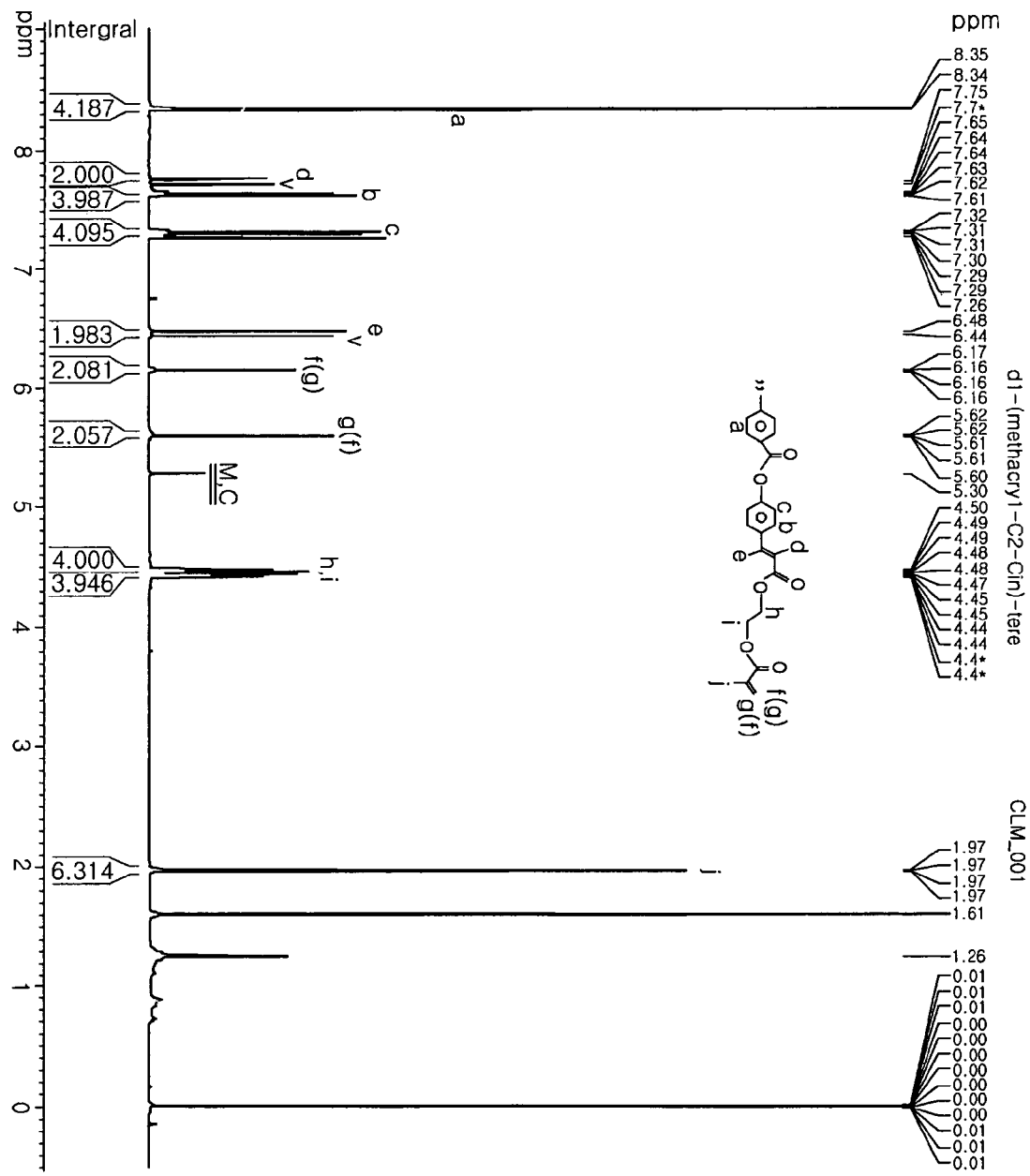

[FIG. 3]
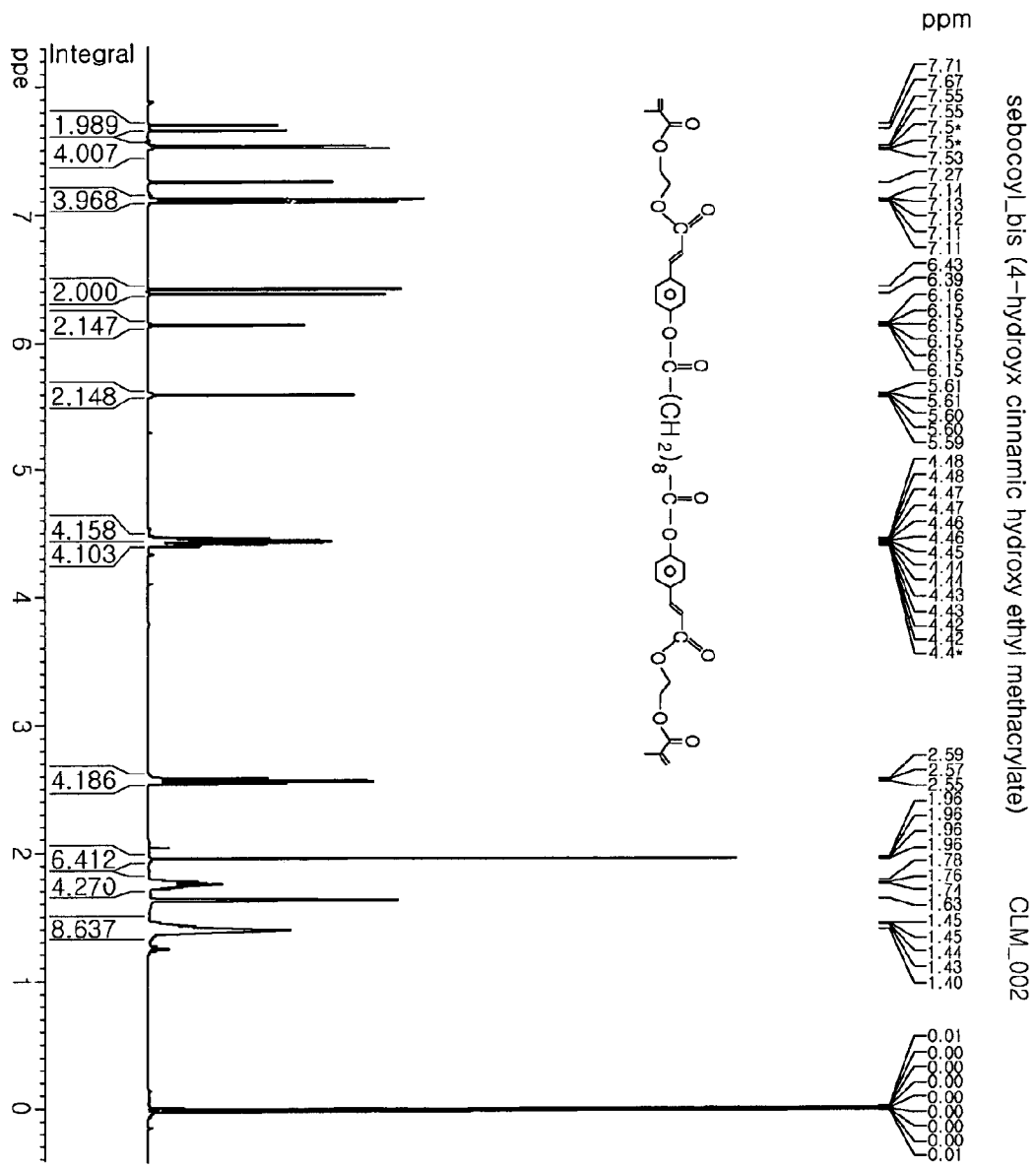

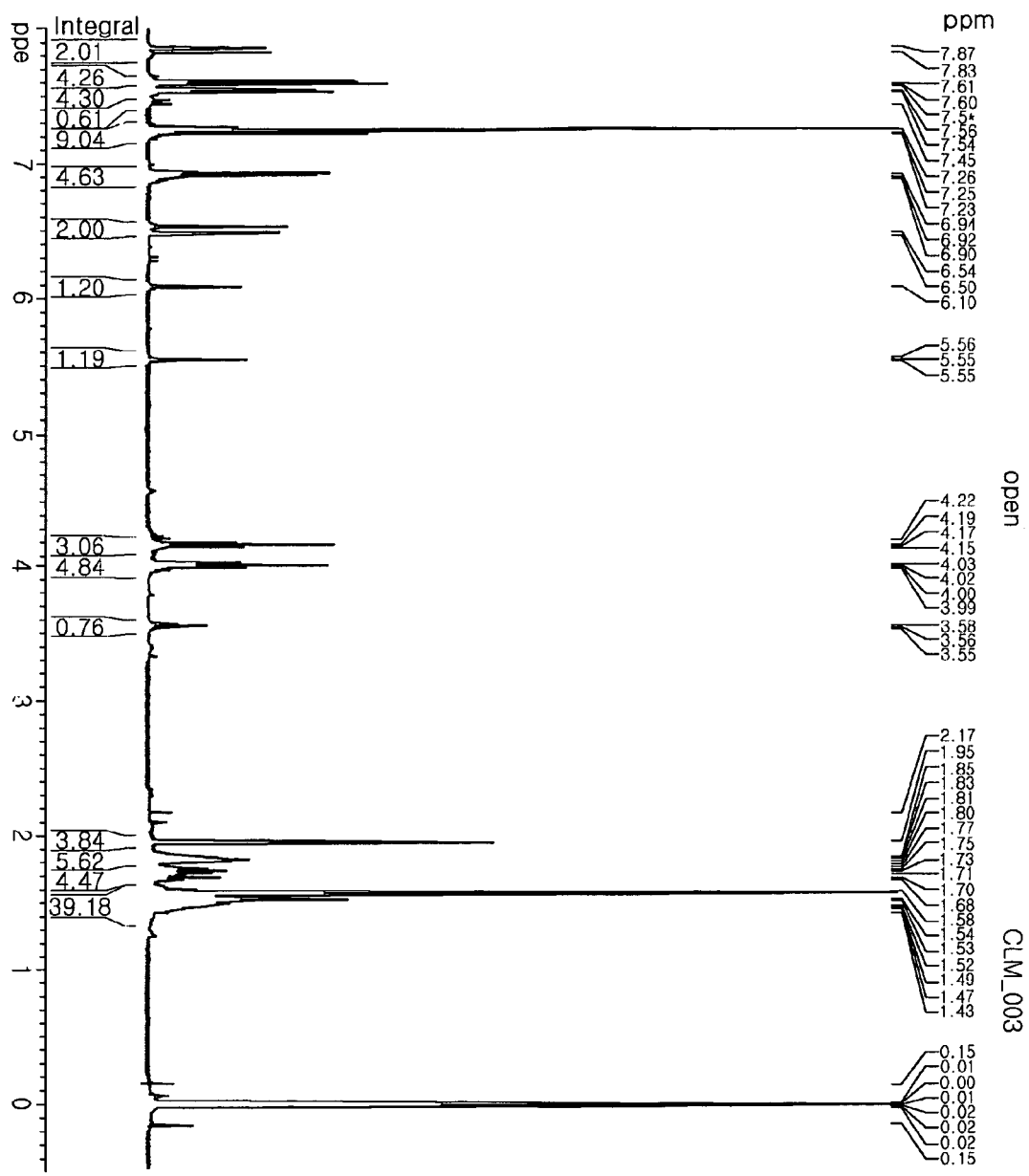
[FIG. 4]

[FIG. 5]
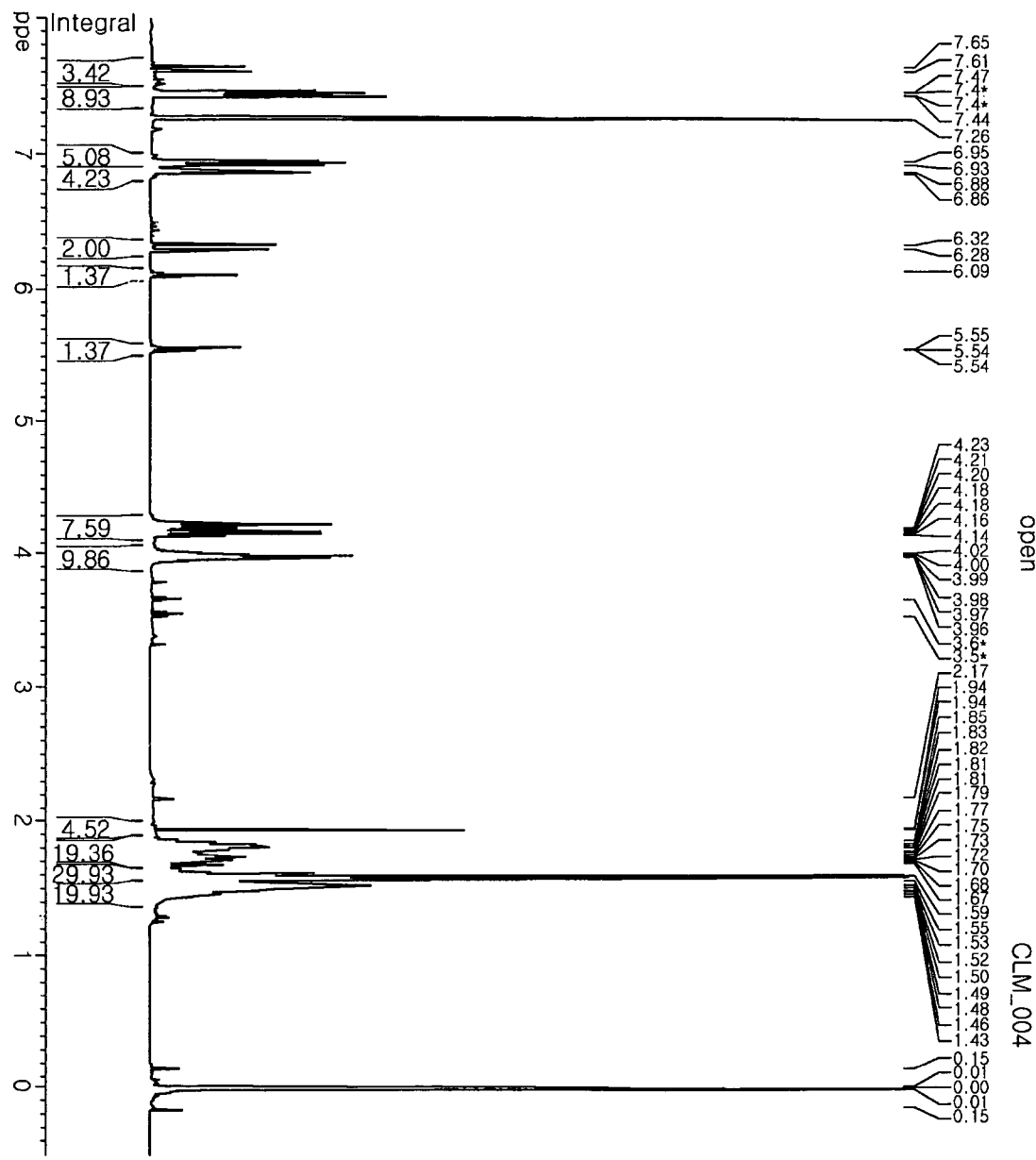

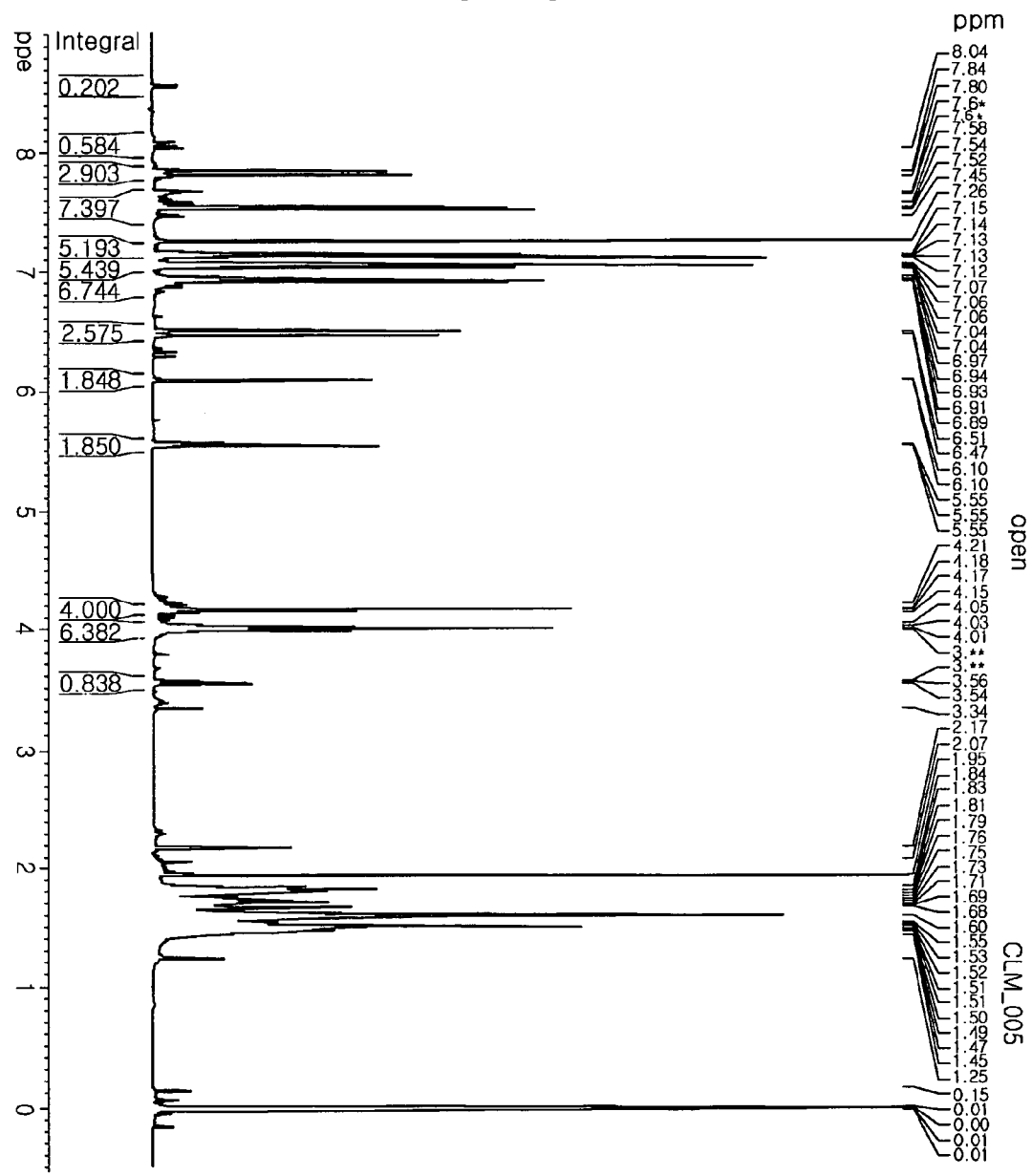
[FIG. 6]

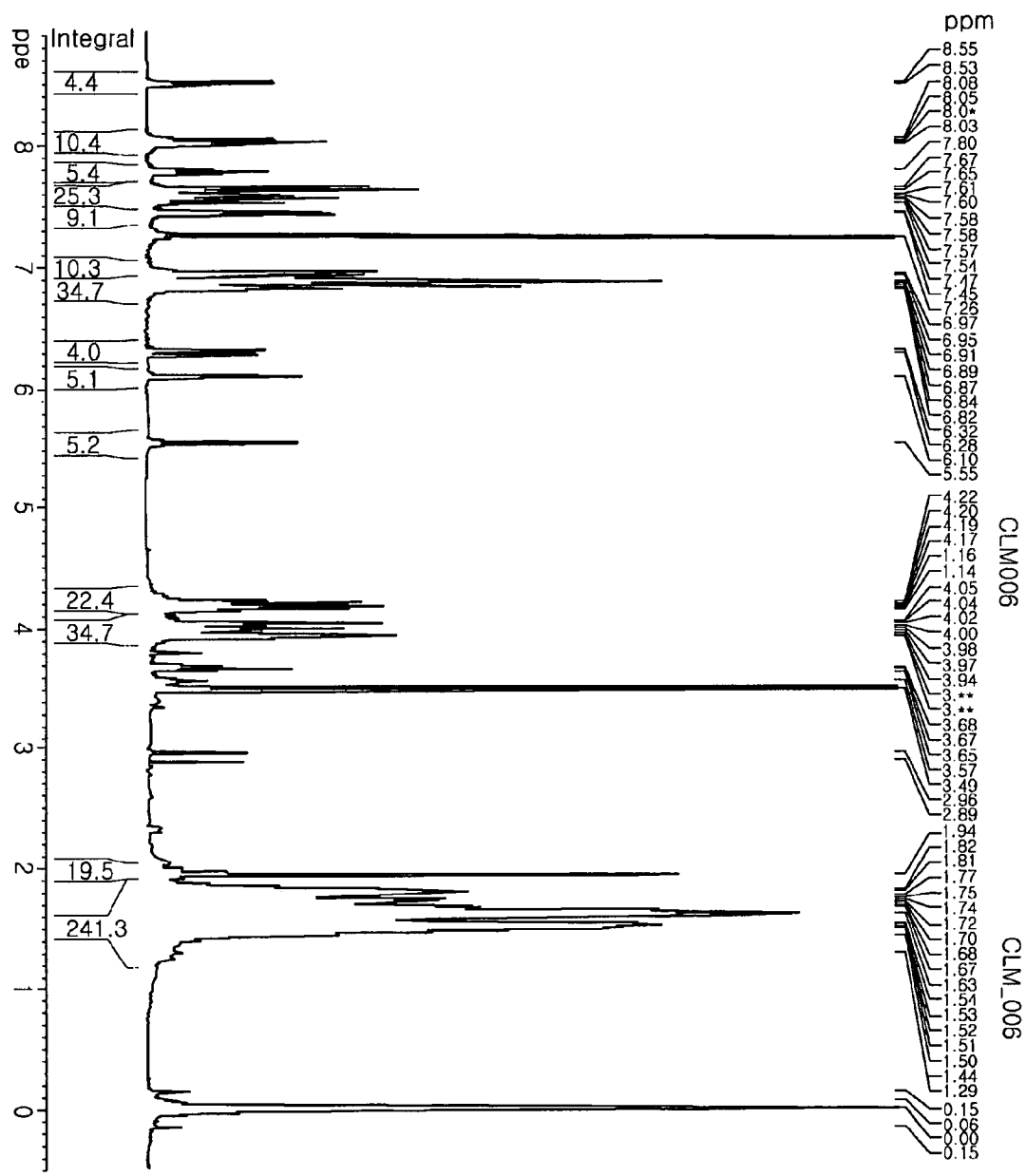
[FIG. 7]

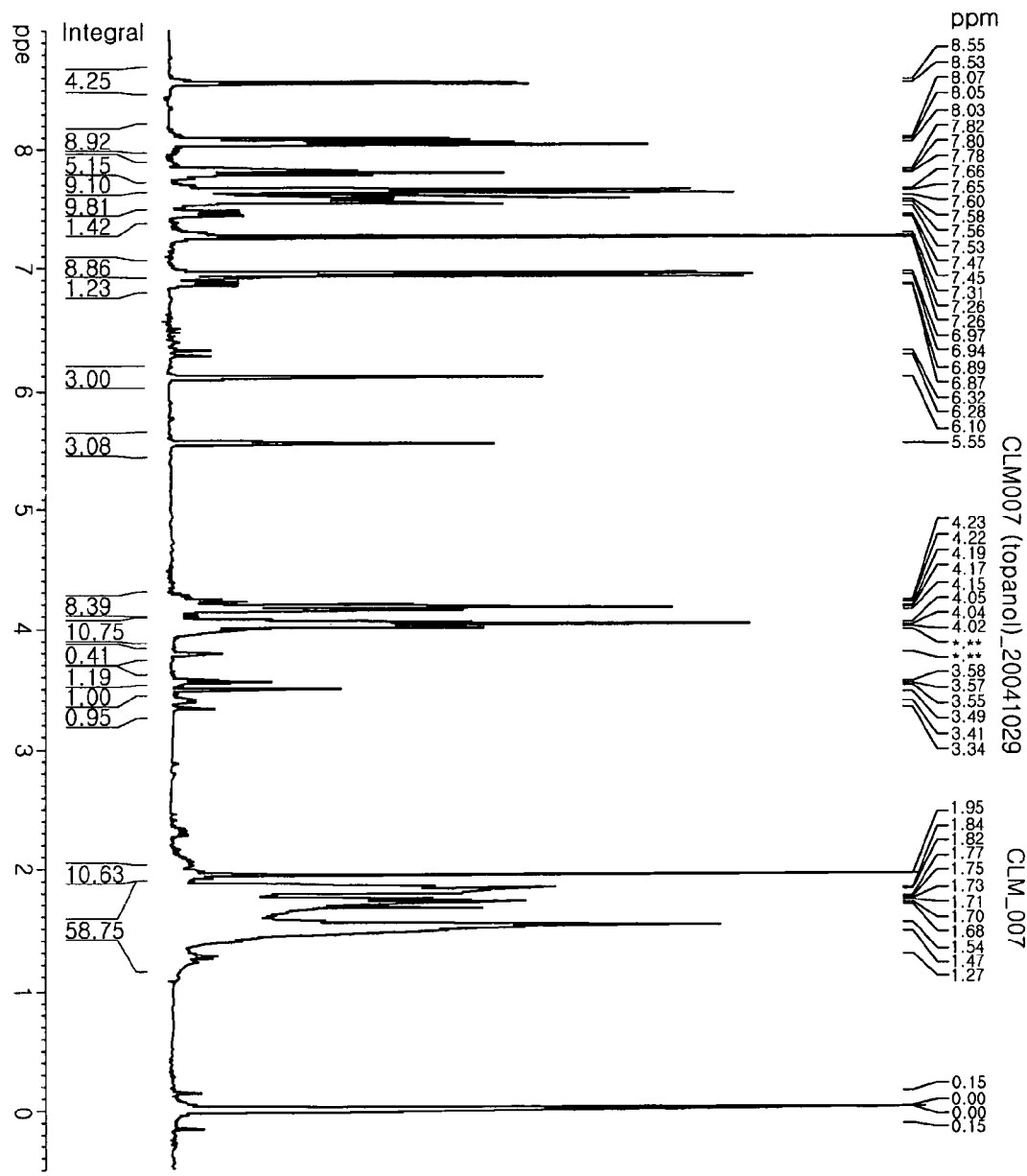
[FIG. 8]

[Fig. 9]
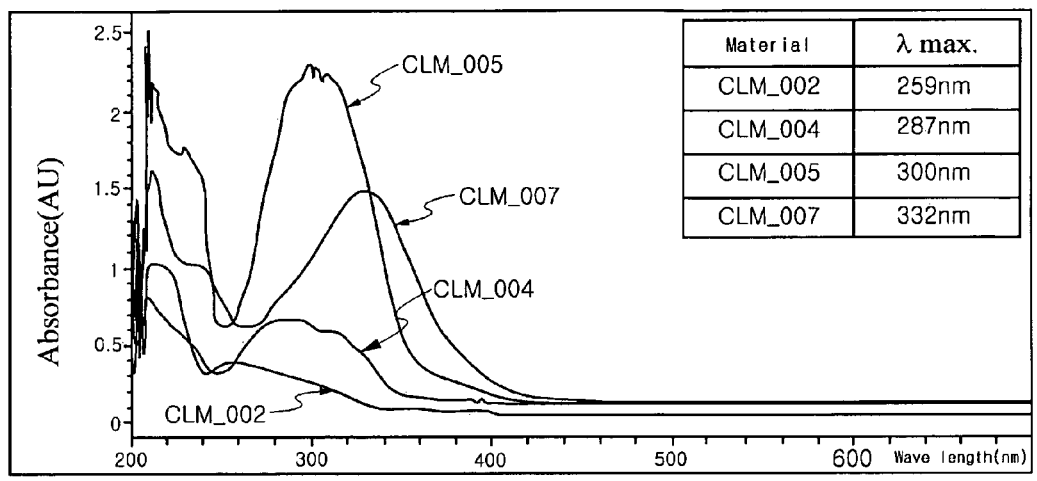
[Figure 10]
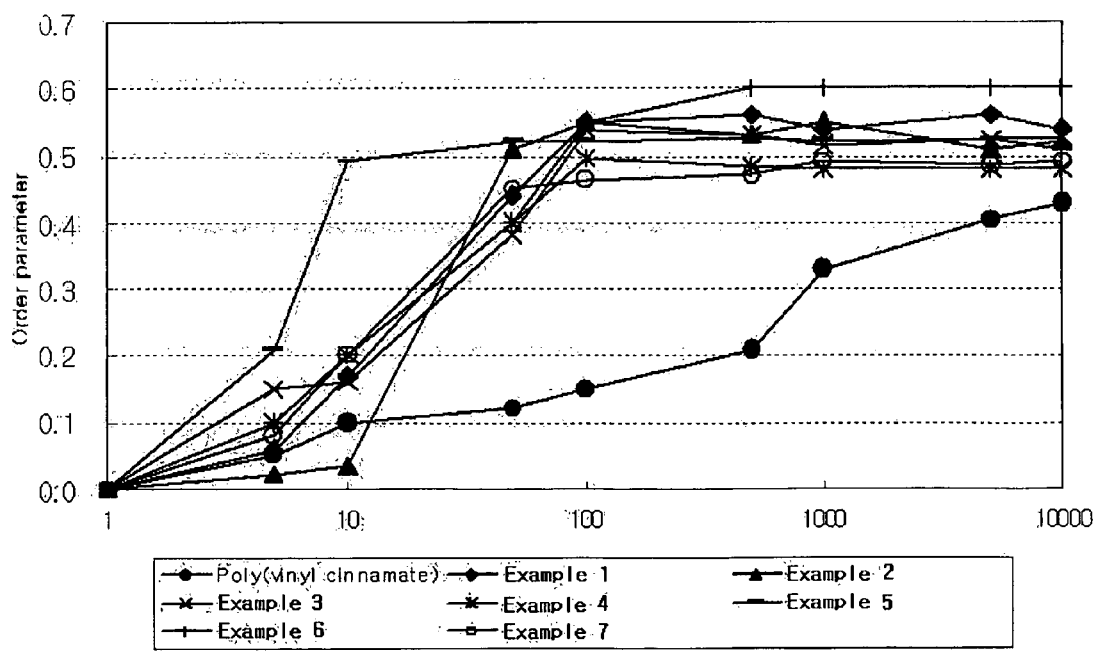

MULTI-FUNCTIONAL MONOMER HAVING A PHOTOREACTIVE GROUP, ALIGNMENT FILM FOR LCD USING THE MONOMER, AND LCD COMPRISING THE ALIGNMENT FILM

This application claims priority to Korean Patent Application No. 10-2005-0088317, filed on Sep. 22, 2005, the disclosure of which is hereby incorporated by reference in its entirety.

TECHNICAL FIELD

The present invention relates to a multi-functional monomer having a photoreactive group and, more particularly, to a multi-functional monomer having a photoreactive group and a heat-curable functional group, an alignment film for LCDs using the multi-functional monomer, and an LCD including the alignment film.

BACKGROUND ART

Currently, it is required that display devices such as televisions and image devices connected to computers are light and slim, and consume a small amount of power. Accordingly, there is a need to produce excellent LCDs in order to obtain flat displays satisfying the above-mentioned requirements.

In the LCD, an alignment film having a surface that is inclined at a pretilt angle is provided to align liquid crystals in a predetermined direction.

With respect to a process of producing the alignment film, a process of rubbing a polymer resin film such as a polyimide resin formed on a substrate using cloths and the like in a predetermined direction, and a process of inclinedly depositing silicon dioxide ($SiO_2$) to produce an alignment film are known. However, in the case of when the alignment film is produced using the rubbing treatment, there are problems in that the yield of products is reduced and contrast deteriorates due to contamination caused by impurities which are generated due to contact during the rubbing and the occurrence of static electricity. Additionally, the process using the inclined deposition is problematic in that production cost is increased and it is difficult to produce the alignment film having the large size, thus obstructing the production of the LCD having the large size.

In order to avoid the above-mentioned problems, currently, a method of producing the alignment film using a transcription process is in the spotlight. In the method of producing the alignment film using the transcription process, a lithograph body, having a surface of which protrusions and recesses to be transcribed are formed, is heated and pressed on a resin film formed on a substrate so as to form the protrusions and the recesses on a surface of the resin film. Generally, the surface of the alignment film, which is produced using the transcription body, has a structure where a plurality of blocks are repetitively formed in parallel on the substrate. However, in the LCD using the alignment film on which only the protrusions and the recesses are formed by the transcription process, the interface regulating force of the liquid crystal is poor and it is impossible to maintain desirable a pretilt angle (generally, 1° or more) by applying the external force or heat. Thus, the so-called domains may be generated.

JP-A-11-181127 discloses a method of producing a polymer-type alignment film that has a main chain including acrylate and methacrylate and a side chain having a photosensitive group such as a cinnamic acid group, and an alignment film produced using the method. However, the polymer is disadvantageous in that, since mobility is poor, it is difficult to obtain desirable alignment properties even though the polymer is exposed to light for a long time. The reason for this is as follows. Since the photosensitive group in the polymer is restrained in the main chain of the polymer, the photosensitive group cannot be rapidly reacted with polarized light when the polarized light is radiated. Accordingly, since it takes a long time to produce a network polymer, process efficiency is reduced. Additionally, if the alignment is finished after the alignment is performed for an insufficient time, the alignment of liquid crystals of the LCD is poor, thus reducing a dichroic ratio and a contrast.

DISCLOSURE

Technical Problem

Therefore, a first object of the invention is to provide a multi-functional monomer that is capable of producing an alignment film designed so that photoreactive groups are rapidly aligned when light is radiated.

A second object of the invention is to provide an alignment film for LCDs using the multi-functional monomer, and a method of producing the same. A third object of the invention is to provide an LCD including the alignment film.

Technical Solution

In order to accomplish the first object of the invention, the invention provides a multi-functional monomer represented by Formula 1:

[Formula 1]

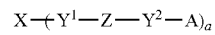

In Formula 1, A is a functional group of Formula 2:

[Formula 2]

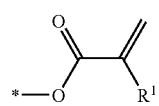

(wherein $R^1$ is hydrogen, a $C_{1-4}$ alkyl or cycloalkyl group), Z is a functional group of Formula 3:

[Formula 3]

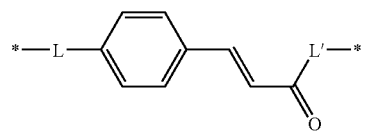

(wherein L and L' are respectively a nitrogen atom or an oxygen atom), $Y^1$ and $Y^2$ are the same as each other or different from each other, and respectively a direct bond or $C_{1-9}$ alkylene, X is a divalent, trivalent, or tetravalent aliphatic, aromatic, or heteroaromatic group, or a ketone, ether or ester group comprising a divalent, trivalent, or tetravalent aliphatic, aromatic, or heteroaromatic group, a is an integer ranging from 2 to 4, and

* denotes a connection portion.

In order to accomplish the second object of the invention, the invention provides an alignment film for an LCD formed using the monomer, and a method of producing the same.

In order to accomplish the third object of the invention, the invention provides an LCD including the alignment film.

DESCRIPTION OF DRAWINGS

FIG. 1 illustrates a liquid crystal display according to the invention;

FIGS. 2 to 8 show NMR analysis results of compounds produced in Examples 1 to 7;

FIG. 9 is a graph showing measurement results of UV-VIS absorbencies of the compounds produced in Examples 2, 4, 5, and 7; and FIG. 10 shows order parameters when polarized light of 365 nm is radiated on the compounds produced in Examples 1 to 7.

BEST MODE

Hereinafter, the invention will be described in detail.

Since a multi-functional monomer according to the invention is applied to a substrate in a monomer state unlike a known photoreactive polymer, a reaction rate of a photoreactive group is very high. Additionally, a typical monomer is problematic in that, since viscosity is low, the monomer is not adsorbed on an inorganic substrate. Accordingly, the multi-functional monomer according to the invention includes a heat-curable functional group as well as the photoreactive group, thus improving physical properties using heat curing.

The invention provides the multi-functional monomer represented by the following Formula 1:

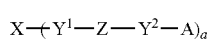

[Formula 1]

In the Formula 1, A, Z, $Y^1$, $Y^2$, X, and a are defined as described above.

In the above-mentioned monomer, the photoreactive group is not restrained in a main chain of polymer unlike a known photoreactive polymer. Thus, since it is possible to perform desirable alignment treatment even though polarized UV is radiated for a short time, the production time and the production cost of the alignment film are reduced and alignment regulating force of liquid crystals is significantly increased, thus increasing a dichroic ratio.

In the case of when the monomer is used along with a photoinitiator generating radicals using radiation of light, photopolymerization occurs. In the case of when a photocuring reaction is performed in conjunction with the alignment treatment of the monomer using the polarized UV, it is possible to improve thermal stability of anisotropy occurring on the alignment film due to polarization. The photocuring and the radiation of the polarized UV may be simultaneously performed, or the photocuring may be performed using additional radiation of light.

In the above-mentioned Formula 1, it is preferable that $Y^1$ and $Y^2$ be functional groups of the following Formula 4:

[Formula 4]

In the above-mentioned Formula 4, p is an integer ranging from 0 to 9.

* denotes a connection portion, and has the same meaning throughout the specification.

In the above-mentioned Formula 1, X is preferably any one of the functional groups represented by the following Formulae 5 to 17, but is not limited thereto.

[Formula 5]

In the above-mentioned Formula 5, n is an integer ranging from 1 to 9.

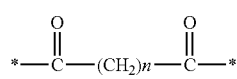

[Formula 6]

In the above-mentioned Formula 6, n is an integer ranging from 1 to 9.

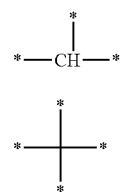

[Formula 7]

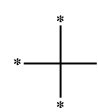

[Formula 8]

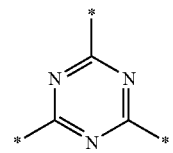

[Formula 9]

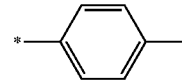

[Formula 10]

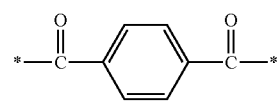

[Formula 11]

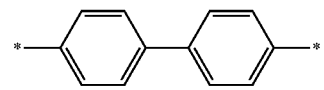

[Formula 12]

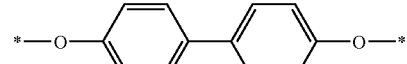

[Formula 13]

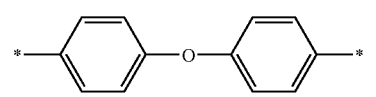

[Formula 14]

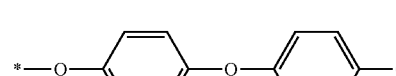

[Formula 15]

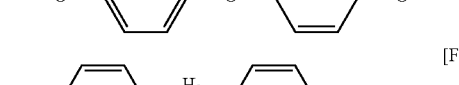

[Formula 16]

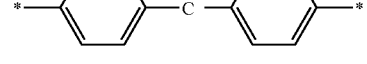

[Formula 17]

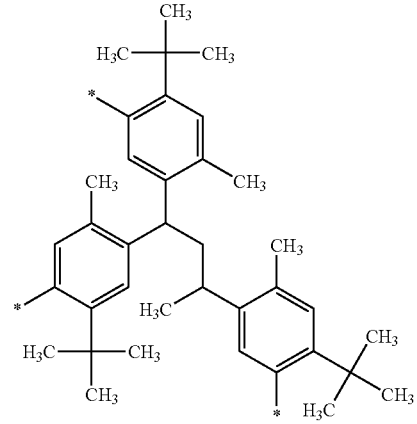

According to an embodiment of the invention, the compound of Formula 1 may be any one of the compounds represented by the following Formulae 18 to 24.

[Formula 18]
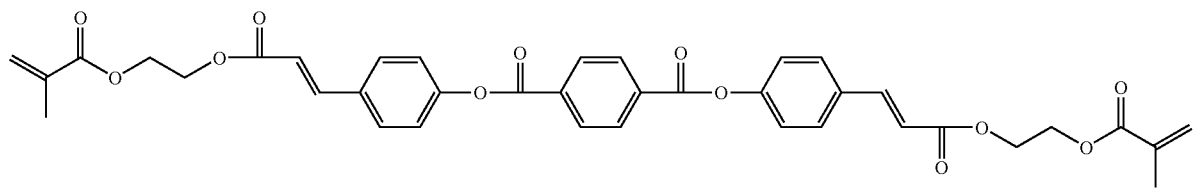
[Formula 19]
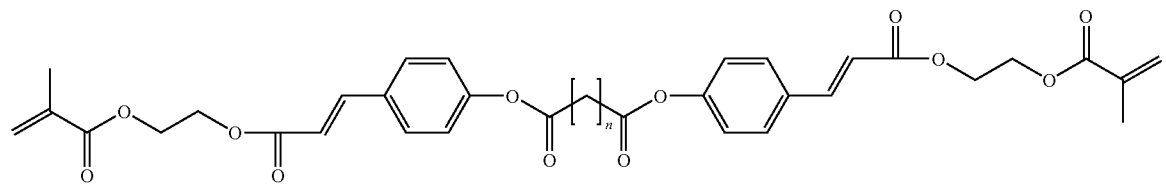
In the above-mentioned Formula 19, n is an integer ranging from 0 to 9.
[Formula 20]
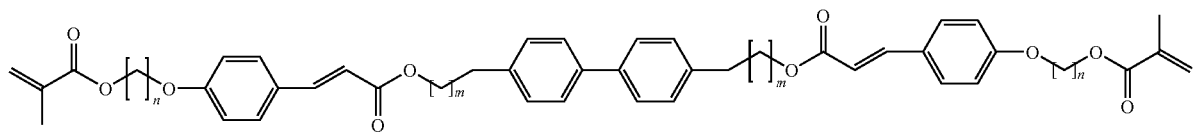
In the above-mentioned Formula 20, m and n are respectively an integer ranging from 0 to 9.
[Formula 21]
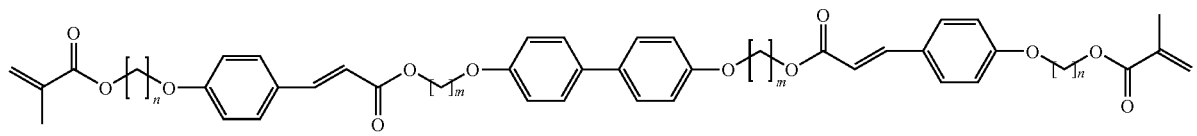
In the above-mentioned Formula 21, m and n are respectively an integer ranging from 0 to 9.
[Formula 22]
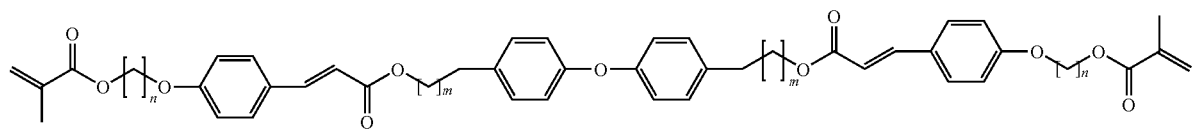

In the above-mentioned Formula 22, m and n are respectively an integer ranging from 0 to 9.

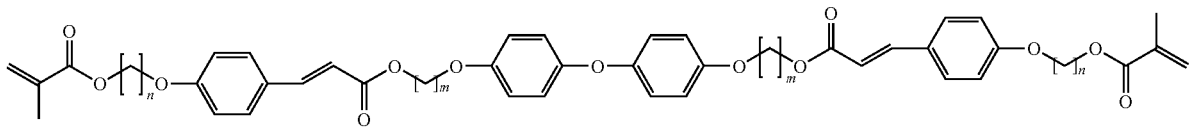

[Formula 23]

In the above-mentioned Formula 23, m and n are respectively an integer ranging from 0 to 9.

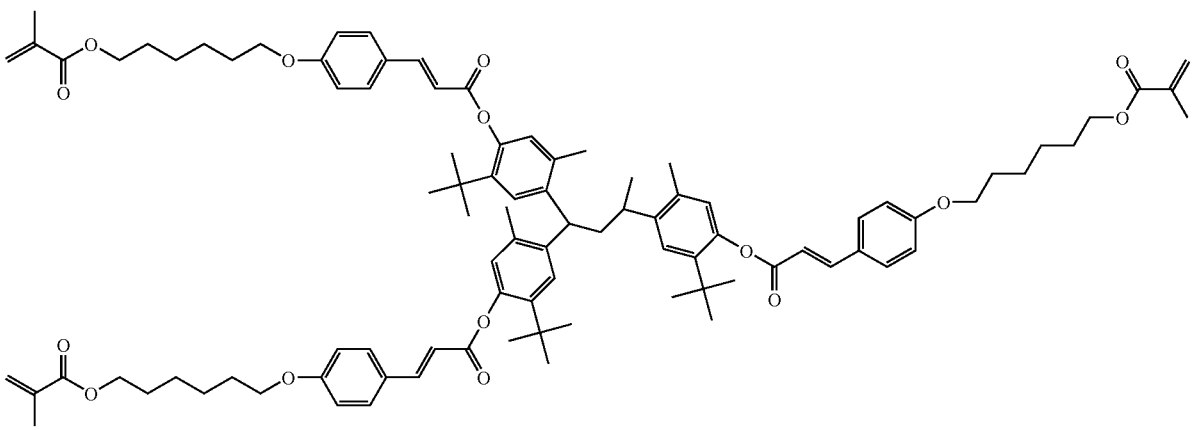

[Formula 24]

The multi-functional monomer generally may be prepared by the following method. A compound comprising the group of Formula 3, $Y^1$ and X is prepared and purified, and then $Y^2$ and A are added and reacted thereto sequentially. The obtained compound, in the amount of equivalents equal to or more than a, is reacted with chlorides or oxides of the center molecule "X" in the presence of catalyst of Lewis bases. However, the above method is only to set forth to illustrate, and starting materials used in the preparation, the order of the reactions, the type of catalysts and specific conditions of the reaction may be changed depending on the structure of compounds.

Furthermore, the invention provides an alignment film for the LCD formed using the multi-functional monomer. The alignment film for LCD according to the invention may be produced by a method comprising the steps of applying a solution where the multi-functional monomer is dissolved on a substrate, removing a solvent from the applied solution to form a film, radiating UV that is polarized in a predetermined direction to provide anisotropy to a surface of the film, and heat treating the film to form a polymer film.

When the solution is prepared, solvents having melting point of 80° C. or more and having excellent solubility to materials that are dissolved in the solvent, such as the multi-functional monomer, are preferably used as a main solvent. Examples of the main solvent include N-methyl pyrrolidone, butyl cellosolve and the like. An additional solvent having solubility properties different from that of the main solvent may be used in small amount, for example less than 20 wt % in the total solvent. Examples of the additional solvent include butyl carbitol. The type of the solvent may be selected variously according to the type of synthesized materials as long as the solvent satisfies the above conditions and the scope of the present invention is not limited to the above examples of solvents. In addition, additives such as a surfactant, adhesive aid and heat-curable initiator, may be used. The total amount of the additives is preferred to 5 wt % or less in the solvent.

Examples of the process of applying the multi-functional monomer solution on the substrate include, but are not limited to a spin coating process, a roll coating process, and a slit coating process. After the multi-functional monomer solution is applied on the substrate, baking treatment may be performed to remove the solvent if necessary.

Next, the substrate on which the multi-functional monomer is applied is exposed to the polarized UV to dimerize a cinnamoyl group or cinnamide group, and heating is performed to polymerize heat-curable functional groups, thereby forming the polymer film. In connection with this, it is preferable that the thickness of the polymer compound film be 100 to 2,000 nm. If the thickness of the polymer compound film is less than 100 nm, thin film diffraction occurs at a predetermined wavelength of visible light, thus reducing transmissivity at a predetermined wavelength. If the thickness of the polymer compound film is more than 2,000 nm, there is a problem in that the transmissivity is reduced due to light absorption of the compound.

The temperature for heat treating is preferably 100° C. to 350° C. The duration for heat treating is preferably 15 minutes to 2 hours. It is preferred that the temperature and duration for heat treating does not exceed 350° C. and 2 hours, respectively. When the temperature and duration for heat treating does not exceed 350° C. and 2 hours, respectively, it becomes problematic in that oxidation of substrates attributable to high temperature or decomposition of materials may occur.

During the production of the alignment film, the photoinitiator is added to the multi-functional monomer solution, and additional radiation of light is performed at the same time the polarized UV is radiated or after the polarized UV is radiated. As described above, the radiation of light may improve thermal stability of anisotropy occurring due to polarized light.

In the present invention, a high-pressure mercury lamp, low-temperature mercury lamp, tungsten light, laser and the like may be used as a light source to generate UV. The intensity of UV area is preferably 5 mW/cm$^2$ or more. The amount of UV radiation is preferably 5 mJ/cm$^2$ or more in order to achieve desirable dimerization properties. The duration for UV radiation is determined according to the required amount of UV radiation and the intensity of light source. Examples of methods for polarizing light include a method of stacking quartz glass substrates, a method of using quartz substrates on which an organic or inorganic thin film is formed, and a method of forming straight patterns on quartz substrates, etc. The degree of light polarization (a value defined by the larger value between the degree of horizontal light polarization and the degree of vertical light polarization divided by small value of the same) is preferably equal to or more than 1.2.

The invention provides an LCD including the alignment film. FIG. 1 illustrates the LCD according to the invention. A shown color LCD 10 includes a pair of substrates 12 and 14 that face each other, liquid crystals 16 inserted between them and sealed, liquid crystal actuating elements 18 formed on the substrate 12, transparent electrodes (pixel electrodes) 20a, 20b, and 20c connected to the liquid crystal actuating elements 18, a counter electrode 22 that is formed on another substrate 14 to face the transparent electrode 20, alignment films 24 supporting liquid crystals 16, polarized light filters (a lower polarized light filter 26 and an upper polarized light filter 28) formed on a pair of substrates 12 and 14, and color filters 30r, 30g, and 30b formed on the substrate 14.

A substrate that is typically used in the LCD may be used as the substrates 12 and 14, and various substrates such as a glass substrate and a ceramic substrate may be used. The shape of the substrate corresponds to that of the commercial LCD, and may be various types including a plane and a rectangle.

The alignment of liquid crystal molecules 16 is changed by application of voltage. For example, in the TN type of liquid crystals shown in FIG. 1, the row of molecules that is distorted at an angle of 90° when voltage is not applied is recovered when voltage is applied to the liquid crystals. Additionally, spacers that are formed of particles are provided between both the alignment films 24 and 24, which is not shown in FIG. 1. The interval between the alignment films between which the liquid crystals are provided is maintained by the spacers.

A thin film transistor (TFT) is used as the liquid crystal actuating element 18, and the liquid crystal actuating element controls voltage applied to the liquid crystals using an actuating signal.

The transparent electrode 20 forms a pair in conjunction with the counter electrode 22 formed on another substrate 14, and applies voltage from the liquid crystal actuating elements 18 to the liquid crystals 16. Generally, an ITO film is used as the transparent electrode. The liquid crystal actuating elements 18 and the transparent electrodes 20a, 20b, and 20c are provided in each pixel, but the counter electrode 22 typically acts as a common electrode of the pixels.

The polarized light filters 26 and 28 are films having the function polarizing straight light, and, in the shown LCD 10, the lower filter 26 and the upper filter 28 formed on the substrates 12 and 14 are set so that a difference in polarization direction is 90°.

The color filter 30 is used in the color LCD, and a set of three color filters having red, green, and blue colors is provided in each pixel. In the color LCD, various colors are realized by combination of the three colors.

Mode for Invention

A better understanding of the present invention may be obtained in light of the following Examples and Comparative Examples which are set forth to illustrate, but are not to be construed to limit the present invention.

EXAMPLE 1

Preparation of Multi-functional Monomer of Formula 18

(1) Preparation of compound (a) [(bis(4-formylphenyl)terephthalate)]

6.6 g of hydroxybenzaldehyde and 10.3 ml of tetraethylamine (TEA) were put into 100 ml of methyl chloride (MC), to which 5 g of terephthalolyl chloride was slowly added dropwise in an ice bath, and the mixture was stirred at the normal temperature for 5 hours. After completion of the reaction, the produced solid in the reaction solution was filtered and washed with MC several times. Thereafter, the resultant was further washed with a 10% aqueous HCl solution and MeOH, and dried in an oven under vacuum to obtain 8.2 g of (bis(4-formylphenyl)terephthalate). (Yield: 89%)

(2) Preparation of compound (b) [1,4-(terephthaloyldioxy)dicinnamic acid)]

5.8 g of bis(4-formylphenyl)terephthalate and 4.84 g of malonic acid were dissolved in 50 ml of pyridine, and 0.1 ml of piperidine was added thereto. The mixture was refluxed for 10 hours. After completion of the reaction, a 10% aqueous HCl solution was added thereto, and the obtained precipitants were filtered and repeatedly washed with water and acetone. Thus obtained solid was dried in an oven under vacuum to obtain 3 g of 1,4-(terephthaloyldioxy)dicinnamic acid). (Yield: 42%)

(3) Preparation of compound of Formula 18

2.7 g of the 1,4-(terephthaloyldioxy) dicinnamic acid was put to 10 ml of SOCl$_2$, about 100 ppm of dimethyl formamide (DMF) was added thereto, and the mixture was refluxed for 2 hours. SOCl$_2$ was removed under reduced pressure, and the residual solid was stirred in 30 ml of pyridine with 6.5 g of 2-hydroxyethyl methacrylate and 100 ppm of N,N-dimethyl-4-aminopyridine (DMAP) at normal temperature for 24 hours. Distilled water was added thereto to complete the reaction, and thus obtained solid was filtered and then purified by column chromatography (MC) to obtain 1.52 g of a pure compound of Formula 18 (CLM_001). (Yield: 38%)

The above-described process is shown in the following Reaction scheme 1.

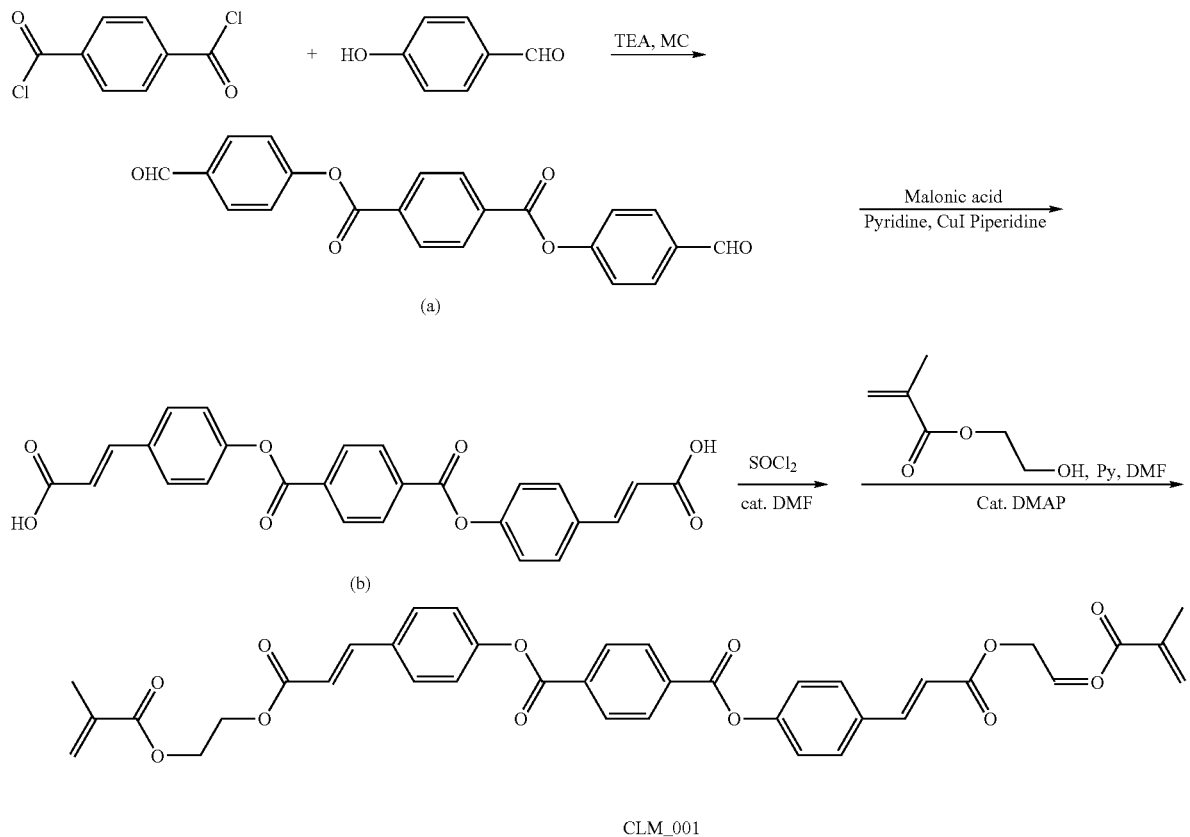

[Reaction scheme 1]

The NMR analysis results carried out in order to confirm the production of the prepared compound of Formula 18 are shown in FIG. 2.

EXAMPLE 2

Preparation of Multi-functional Monomer of Formula 19

(1) Preparation of compound (c) [(bis(4-formylphenyl) sebacoylate)]

10.25 g of hydroxybenzaldehyde and 12.8 ml of TEA were put to 200 ml of MC, to which 11.19 g of sebacoyl chloride was slowly added dropwise in an ice bath, and the mixture was stirred at normal temperature for 5 hours. After completion of the reaction, a 10% aqueous HCl solution was added thereto to wash the MC layer, and deionized water was used to further wash the organic layer. The organic layer was dried over $MgSO_4$, and concentrated under reduced pressure to obtain 15.7 g of crude bis(4-formylphenyl) sebacoylate. (Yield: 100%)

(2) Preparation of compound (d) [1,4-(sebacoyldioxy) dicinnamic acid)]

3 g of bis(4-formylphenyl)sebacoylate and 2.3 g of malonic acid were dissolved in 30 ml of pyridine, to which 0.1 ml of piperidine was put, and the mixture was refluxed for 10 hours. After completion of the reaction, a 10% aqueous HCl solution was added thereto, and thus produced precipitates were filtered, and washed with deionized water and acetone several times. Thus obtained solid was dried in an oven under vacuum to 2.35 g of 1,4-(sebacoyldioxy)dicinnamic acid. (Yield: 65%)

(3) Preparation of compound of Formula 19

2.6 g of 1,4-(sebacoyldioxy) dicinammic acid was put to 25 ml of $SOCl_2$, to which about 100 ppm of DMF was added, and the mixture was refluxed for 2 hours. $SOCl_2$ was removed under reduced pressure, and the residual solid was stirred in 30 ml of pyridine with 3.84 ml of 2-hydroxyethyl methacrylate and about 100 ppm of DMAP at normal temperature for 24 hours. Distilled water was added thereto to complete the reaction, and thus obtained solid was filtered and then purified by column chromatography (MC) to obtain 1.9 g of a compound of Formula 19 (CLM_002). (Yield: 50%)

The above-described process is shown in the following Reaction scheme 2.

[Reaction scheme 2]

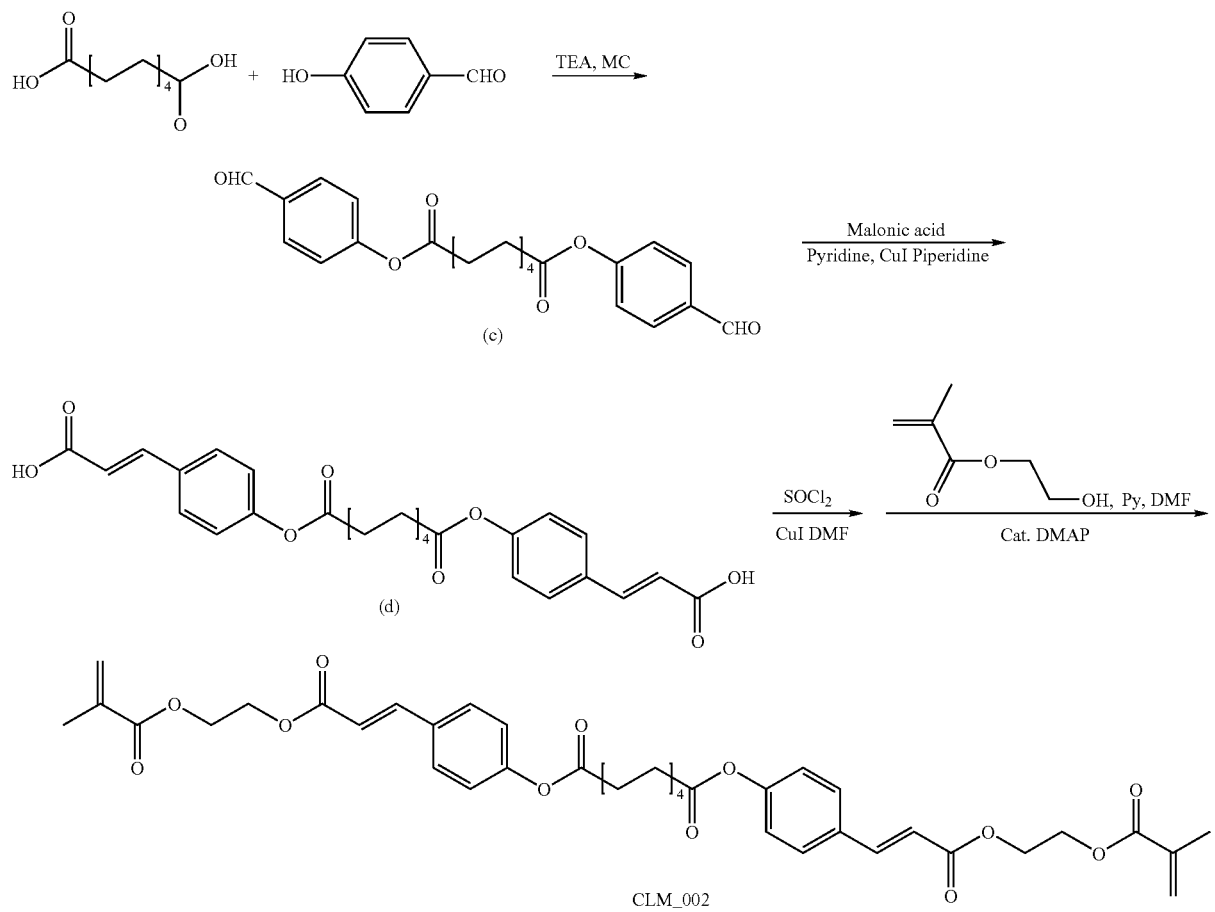

The NMR analysis results carried out in order to confirm the production of the prepared compound of Formula 19 are shown in FIG. 3.

EXAMPLE 3

Preparation of Multi-functional Monomer of Formula 20

(1) Preparation of compound (e) [4-((6-hydroxy-hexyl)oxy)cinnamon acid)]

A solution of 4.4 g of NaOH in 20 ml of distilled water was added to a solution of 7.5 g of 4-hydroxy cinnamic acid in methanol, 0.02 g of KI was added thereto, and then 10.0 g of 6-bromo-1-hexanol was slowly added dropwise for reaction at 65° C. for 24 hours. 100 ml of distilled water was added thereto to complete the reaction, and then the mixture was cooled to normal temperature. A 10% aqueous HCl solution was added thereto, and the obtained precipitants were filtered to obtain 9.5 g of 4-((6-hydroxyhexyl)oxy)cinnamic acid. (Yield: 60%)

(2) Preparation of compound (f) [4-((6-(Methacroy-loxy)hexyl)oxy)cinnamic acid]

To a solution of 4.6 g of 4-((6-hydroxyhexyl)oxy)cinnamic acid and 4.4 ml of pyridine in 30 ml of DMF, 5.9 ml of methacryloyl chloride was slowly added dropwise, and then dimethyl aminopyridine was added portionwise thereto. The mixture was stirred at normal temperature for 24 hours. After completion of the reaction, a 10% aqueous HCl solution was added thereto, and the obtained precipitants were filtered and recrystallized from methanol to obtain 3 g of 4-((6-(methacroyloxy) hexyl)oxy)cinnamic acid). (Yield: 50%)

(3) Preparation of compound of Formula 20

0.35 g of 4,4'-biphenol and 1.5 g of 4-((6-(methacroyloxy) hexyl)oxy)cinnamic acid were dissolved in 25 ml of DMF, to which 1.15 g of 1-(3-dimethylaminopropyl)-3-ethylcarbodi-imide and 0.76 g of 1-hydroxybenzotrizole were added, and further 1.15 ml of triethylamine for reaction at normal temperature for 24 hours. Distilled water was added thereto to complete the reaction, and the mixture was stirred for 30 minutes, and the precipitant was filtered and washed with methanol several times. This filtrate was recrystallized from methanol to obtain 1.2 g of a compound of Formula 20 (CLM_003). (Yield: 60%)

The above-described process is shown in the following Reaction scheme 3.

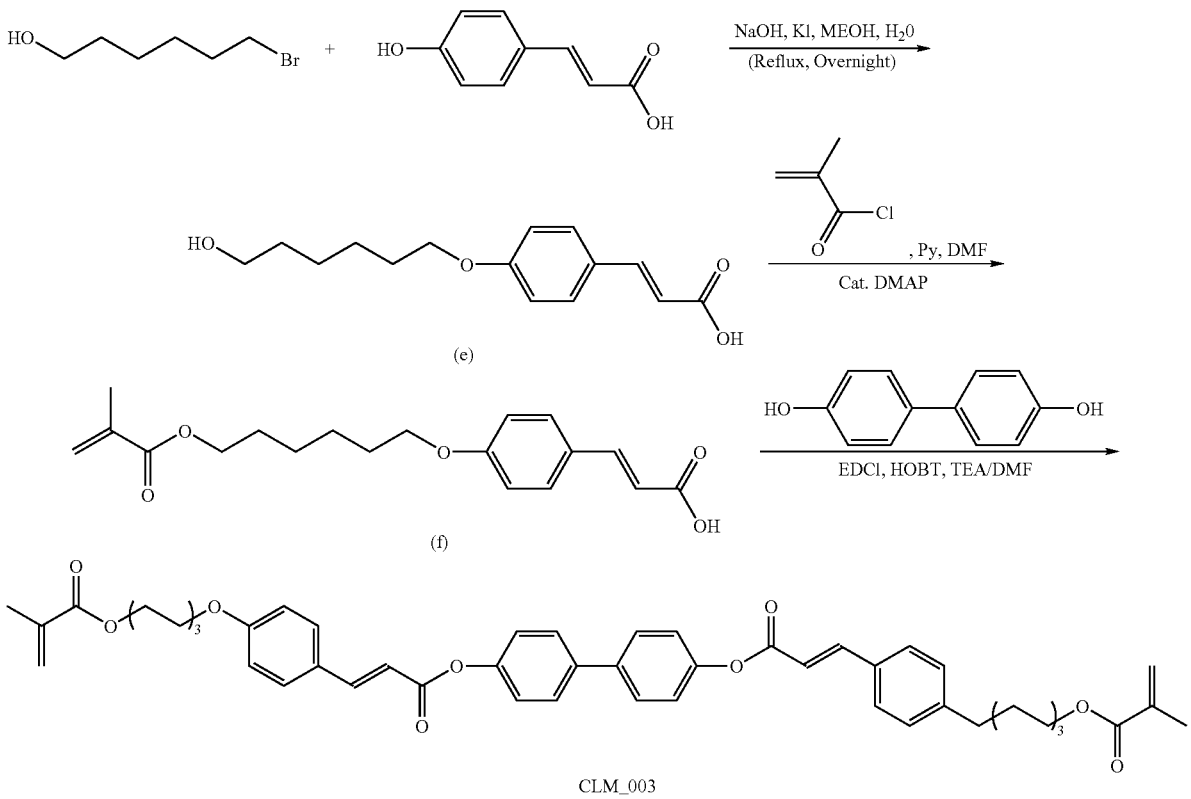

The NMR analysis results carried out in order to confirm the production of the prepared compound of Formula 20 are shown in FIG. 4.

EXAMPLE 4

Preparation of Multi-functional Monomer of Formula 21

(1) Preparation of compound (g) [4,4'-(di(6-hydroxyhexyl)oxy)biphenyl]

To a solution of 3 g of 4,4'-biphenol and 18 g of $K_2CO_3$ in methylethylketone (MEK), 0.02 g of KI was put, and 6.9 g of 6-bromo-1-hexanol was slowly added dropwise thereto for reaction at 80° C. for 24 hours. 100 ml of distilled water was added thereto to complete the reaction, the mixture was cooled to normal temperature, and a 10% aqueous HCl solution was added thereto. The obtained precipitants were filtered to obtain 3.8 g of 4,4'-(di(6-hydroxyhexyl)oxy))biphenyl. (Yield: 50%)

(2) Preparation of compound of Formula 21

To solution of 0.73 g of 4,4'-(di(6-hydroxyhexyl)oxy))biphenyl and 1.5 g of the compound (f) of Example 3, 4-((6-(methacroyloxy)hexyl)oxy)cinnamic acid in 25 ml of DMF, 1.15 g of 1-(3-dimethylaminopropyl)-3-ethylcarbodiimide and 0.76 g of 1-hydroxybenzotrizole were put, and 1.15 ml of triethylamine was added thereto for reaction at normal temperature for 24 hours. Distilled water was added thereto to complete the reaction, the mixture was stirred for 30 minutes, and the precipitant was filtered and washed with methanol several times. This filtrate was recrystallized from methanol to obtain 1.0 g of the compound of Formula 21 (CLM_004). (Yield: 40%)

The above-described process is shown in the following Reaction scheme 4.

[Reaction scheme 4]

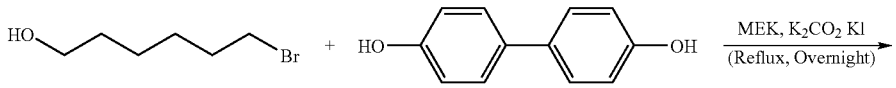

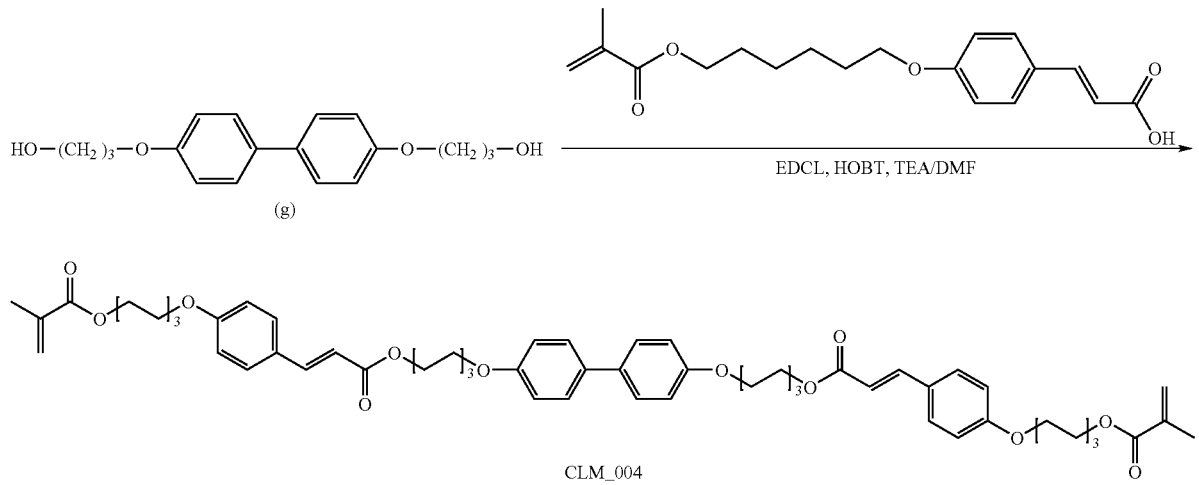

CLM_004

The NMR analysis results carried out in order to confirm the production of the prepared compound of Formula 21 are shown in FIG. 5.

EXAMPLE 5

Preparation of Multi-functional Monomer of Formula 22

To a solution of 0.30 g of 4,4'-(dihydroxydiphenyl ether and 1.2 g of the compound (f) of Example 3, 4-((6-(methacroyloxy)hexyl)oxy)cinnamic acid in 25 ml of DMF, 0.92 g of 1-(3-dimethylaminopropyl)-3-ethylcarbodiimide and 0.60 g of 1-hydroxybenzotrizole was put, and 0.91 ml of triethylamine was added thereto for reaction at normal temperature for 24 hours. Distilled water was added thereto to complete the reaction, and the mixture was stirred for 30 minutes, and the precipitant was filtered and washed with methanol several times. This filtrate was recrystallized from methanol to obtain 1.1 g of the compound of Formula 22 (CLM_005). (Yield: 70%)

The above-described process is shown in the following Reaction scheme 5.

[Reaction scheme 5]

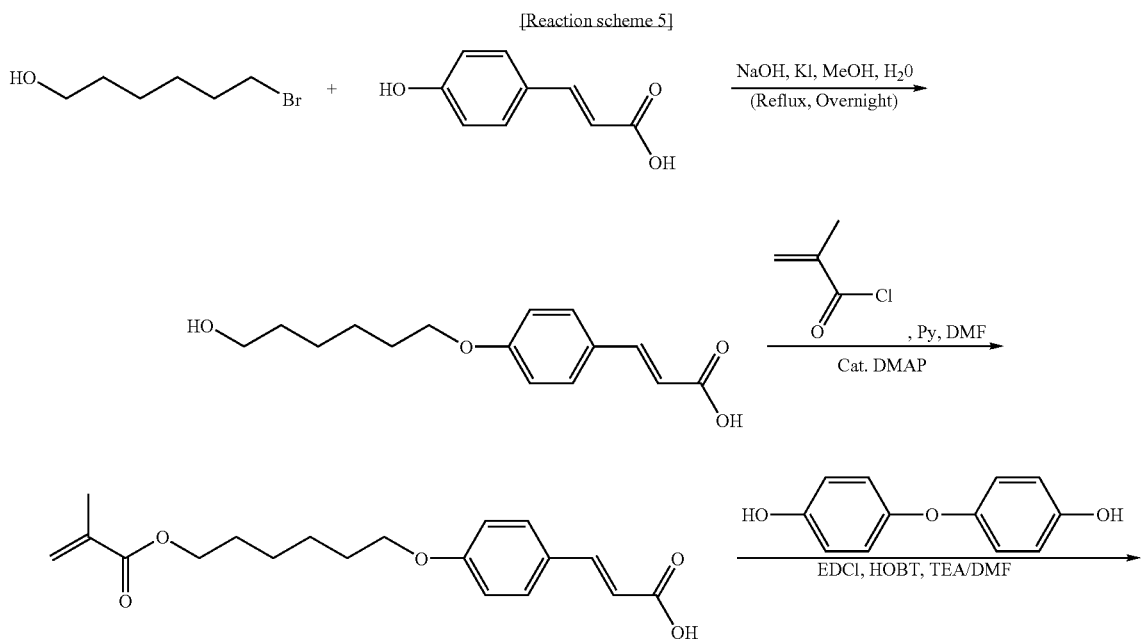

-continued

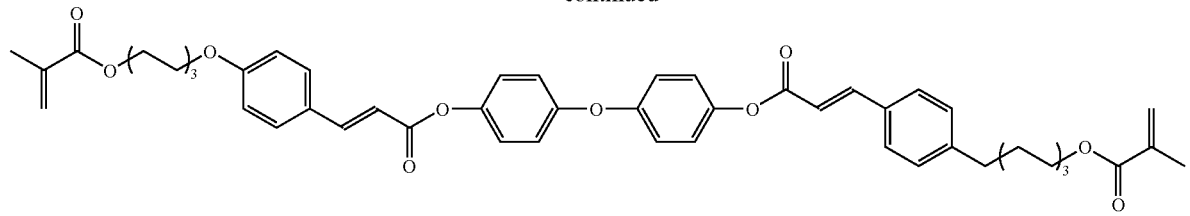

CLM_005

EXAMPLE 6

Preparation of Multi-functional Monomer of Formula 23

To a solution of 0.60 g of 4,4'-(di(6-hydroxyhexyl)oxy)diphenyl ether and 1.2 g of the compound (f) of Example 3, 4-((6-(methacroyloxy)hexyl)oxy)cinnamic acid in 25 ml of DMF, 0.92 g of 1-(3-dimethylaminopropyl)-3-ethylcarbodiimide and 0.61 g of 1-hydroxybenzotrizole were put, and 0.91 ml of triethylamine was added thereto for reaction at normal temperature for 24 hours. Distilled water was added thereto to complete the reaction, and the mixture was stirred for 30 minutes, and the precipitant was filtered and washed with methanol several times. This filtrate was recrystallized from methanol to obtain 1.2 g of the compound of Formula 23 (CLM__006). (Yield: 62%)

The above-described process is shown in the following Reaction scheme 6.

The NMR analysis results carried out in order to confirm the production of the prepared compound of Formula 22 are shown in FIG. 6.

The NMR analysis results carried out in order to confirm the production of the prepared compound of Formula 23 are shown in FIG. 7.

EXAMPLE 7

Preparation of Multi-functional Monomer of Formula 24

To a solution of 0.46 g of 1,1,3-tris(2-methyl-4-hydroxy-5-tert-butylphenyl)butane and 1 g of the compound (f) of Example 3, 4-((6-(methacroyloxy)hexyl)oxy)cinnamic acid in 20 ml of DMF, 0.77 g of 1-(3-dimethylaminopropyl)-3-ethylcarbodiimide and 0.51 g of 1-hydroxybenzotrizole were put, and 0.8 ml of triethylamine was added thereto for reaction at normal temperature for 24 hours. Distilled water was added thereto to complete the reaction, and the mixture was stirred for 30 minutes, and the precipitant was filtered and washed with methanol several times. This filtrate was recrystallized from MC/n-hexane to obtain 0.8 g of the compound of Formula 24 (CLM__007). (Yield: 70%)

The above-described process is shown in the following Reaction scheme 7.

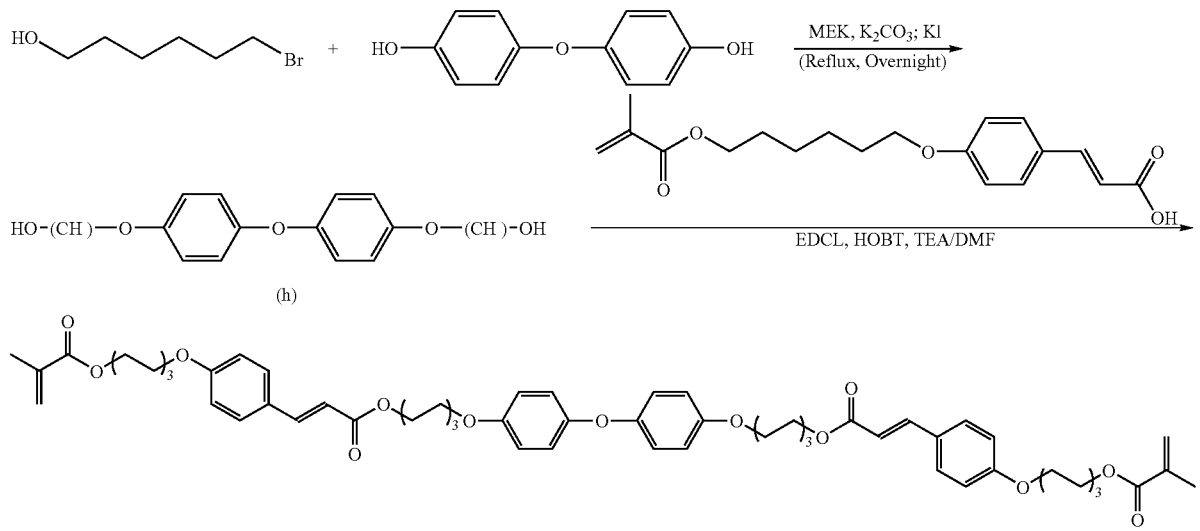

CLM_006

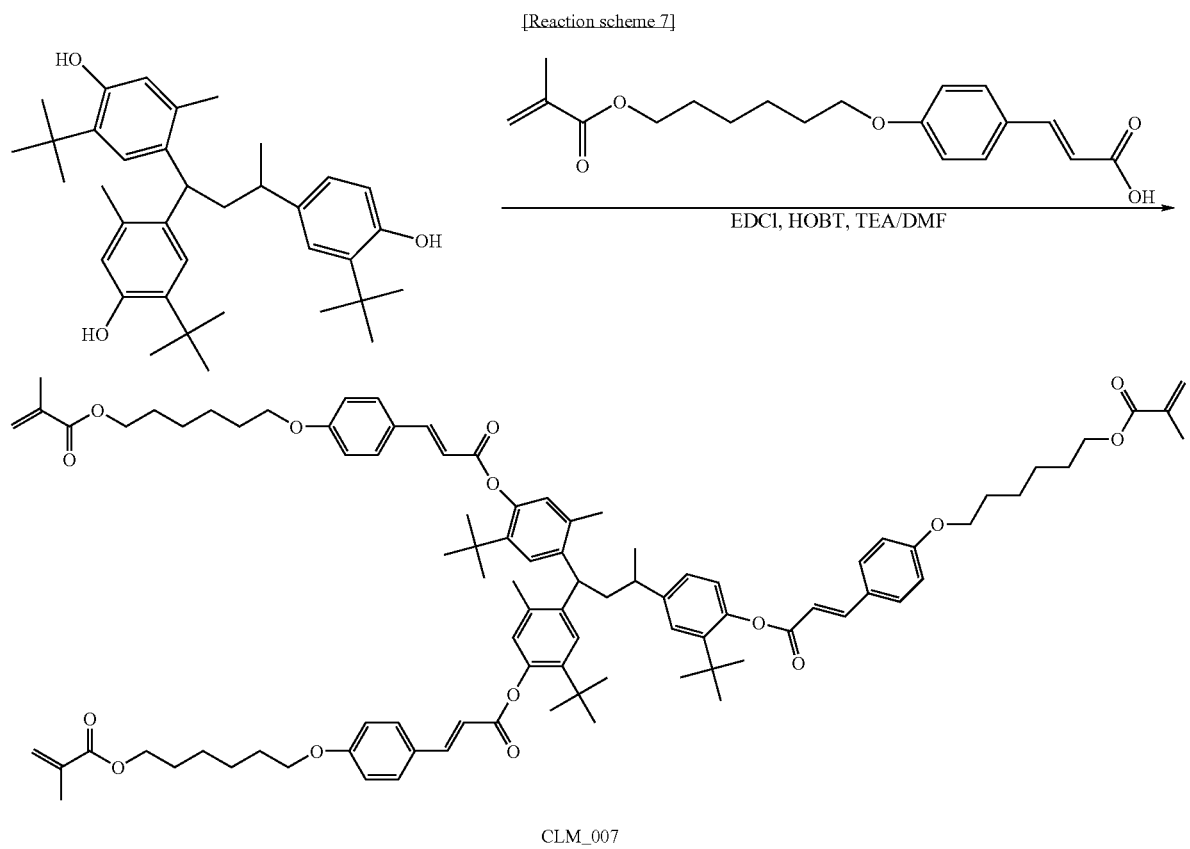

CLM_007

The NMR analysis results carried out in order to confirm the production of the prepared compound of Formula 24 are shown in FIG. 8.

EXAMPLES 8 to 11

Production and Properties of the Alignment Film

To obtain optical properties of the substances of Examples 2, 4, 5, and 7 (CLM_002, 004, 005, and 007), UV-VIS absorbencies were measured. In order to achieve this, a solution in which the sample was dissolved in cyclopentanone was applied on a quartz substrate using spin coating to form a thin film, and the thin film was dried on a hot plate at 150° C. for 2 min to remove a solvent. The thickness of the film was 110 nm. The results are shown in FIG. 9. From FIG. 9, it can be seen that the monomers of Examples reacted with light having the wavelength of 260 to 330 nm.

Further, in order to evaluate thermal properties of the compounds produced in Examples 1 to 7, heat absorption and generation temperatures were checked using DSC data. Melting temperatures were found on the DSC curves of all substances, and heat generation was observed while the first heating was performed. The heat generation peak was observed at 140 to 250° C. during the first heating, which depended on the molecular structure. Accordingly, it is believed that crosslinking of acrylate occurred. The DSC test results are described in the following Table 1.

TABLE 1

| | First heating | | First cooling | Second heating |
|---|---|---|---|---|
| | heat absorption (° C.) | heat generation (° C.) | heat generation (° C.) | heat absorption (° C.) |
| Example 1 | 73, 140 | 146 | 69 | 72 |
| Example 2 | 80 | 175 | — | — |
| Example 3 | 130 | 143 | 105 | 130 |
| Example 4 | 76 | 211 | 56 | 77 |
| Example 5 | 93, 103 | 208, 239 | 74 | 95 |
| Example 6 | 126 | 161, 220 | — | — |
| Example 7 | 88 | 219 | 71 | — |

Polarized light was radiated using the film which was produced through the above-mentioned procedure to align the liquid crystals, thereby producing the parallel liquid crystal cell.

In order to evaluate the degree of alignment of the liquid crystals, the order parameter S using transmissivity of polarized light was calculated through the following Equation 1.

$$S = \frac{A_1 - A_2}{A_1 + 2A_2} \qquad \text{[Equation 1]}$$

In Equation 1, A1 and A2 denote transmissivities when polarization and alignment directions are identical and perpendicular to each other.

The order parameters when polarized light of 365 nm was radiated on the compounds of Examples 1 to 7 in a predetermined dose to produce the liquid crystal cells are shown in FIG. 10. Poly(vinyl cinnamate) was used for comparison with the polymer in views of reactivity. From FIG. 10, it can be seen that the order parameter of the polymer was increased even though light of 10000 mJ was radiated. However, in the case of the multi-functional monomer of the invention, saturation was achieved at 100 mJ.

To observe the change in thermal stability of the film due to additional photoreaction, the liquid crystal cells that were produced by radiating polarized light of 365 nm in the intensity of 100 mJ and 1000 mJ to the substances were left at 150° C. for 30 min and for 1 hour to measure the order parameters.

In order to evaluate the results obtained from the additional photoreaction using the photoinitiator, 1 mass % of the photoinitiator (Irgacure 369, absorption wavelength of about 305 nm) was added to the substance, exposure was performed using polarized light of 365 nm having the intensity of 100 mJ, and additional exposure was performed using light of 305 nm that was not polarized in the intensity of 100 mJ and 1000 mJ. The liquid crystal cells were left at 150° C. for 30 min and for 1 hour, and the order parameters were measured. Reduction in the order parameter for the above-mentioned cases is shown in the following Table 2.

TABLE 2

| SAMPLE | 365 nm Polarization dose (mJ) | 305 nm add. (mJ) | 150° C. (0 min) | 150° C. (30 min) | 150° C. (60 min) | Ratio (%) |
|---|---|---|---|---|---|---|
| Example 1 | 100 | 0 | 0.55 | 0.22 | 0.08 | 14 |
|  | 1000 | 0 | 0.54 | 0.33 | 0.22 | 40 |
|  | 100 | 100 | 0.52 | 0.44 | 0.39 | 76 |
|  | 100 | 1000 | 0.50 | 0.48 | 0.45 | 90 |
| Example 2 | 100 | 0 | 0.55 | 0.22 | 0.08 | 15 |
|  | 1000 | 0 | 0.55 | 0.34 | 0.23 | 41 |
|  | 100 | 100 | 0.52 | 0.43 | 0.39 | 75 |
|  | 100 | 1000 | 0.51 | 0.48 | 0.46 | 91 |
| Example 3 | 100 | 0 | 0.54 | 0.21 | 0.08 | 14 |
|  | 1000 | 0 | 0.52 | 0.31 | 0.20 | 40 |
|  | 100 | 100 | 0.48 | 0.40 | 0.36 | 76 |
|  | 100 | 1000 | 0.45 | 0.43 | 0.41 | 90 |
| Example 4 | 100 | 0 | 0.50 | 0.19 | 0.07 | 14 |
|  | 1000 | 0 | 0.48 | 0.29 | 0.20 | 41 |
|  | 100 | 100 | 0.47 | 0.38 | 0.35 | 74 |
|  | 100 | 1000 | 0.44 | 0.42 | 0.40 | 91 |
| Example 5 | 100 | 0 | 0.52 | 0.21 | 0.08 | 15 |
|  | 1000 | 0 | 0.52 | 0.31 | 0.20 | 39 |
|  | 100 | 100 | 0.48 | 0.39 | 0.36 | 74 |
|  | 100 | 1000 | 0.47 | 0.45 | 0.42 | 90 |
| Example 6 | 100 | 0 | 0.55 | 0.22 | 0.08 | 14 |
|  | 1000 | 0 | 0.60 | 0.36 | 0.24 | 40 |
|  | 100 | 100 | 0.50 | 0.41 | 0.37 | 74 |
|  | 100 | 1000 | 0.53 | 0.50 | 0.47 | 90 |
| Example 7 | 100 | 0 | 0.47 | 0.19 | 0.07 | 16 |
|  | 1000 | 0 | 0.50 | 0.30 | 0.20 | 41 |
|  | 100 | 100 | 0.44 | 0.36 | 0.33 | 75 |
|  | 100 | 1000 | 0.46 | 0.43 | 0.41 | 89 |

From Table 2, it can be seen that the change in anisotropy due to heat is reduced as the radiation time of the polarized light is increased and the additional exposure time is increased.

Although the present invention has been described in connection with the exemplary embodiments of the present invention, it will be apparent to those skilled in the art that various modifications and changes may be made thereto without departing from the scope and spirit of the invention. Therefore, it is to be understood that within the scope of the appended claims, the invention may be practiced otherwise than as specifically described.

INDUSTRIAL APPLICABILITY

As described above, in a multi-functional monomer according to the invention, a photoreactive group is not restrained in a main chain of a polymer. Thus, since it is possible to perform desirable alignment treatment even though polarized UV is radiated for a short time, the production time and the production cost are reduced and alignment regulating force of liquid crystals is increased, thereby increasing a dichroic ratio. Furthermore, since the multi-functional monomer includes a heat-curable functional group, it is possible to improve physical properties by additional photocuring in conjunction with the alignment.

The invention claimed is:

1. A multi-functional monomer represented by Formula 1:

[Formula 1]

wherein A is a functional group of Formula 2:

[Formula 2]

(wherein $R_1$ is hydrogen, a $C_{1-4}$ alkyl or cycloalkyl group) Z is a functional group of Formula 3:

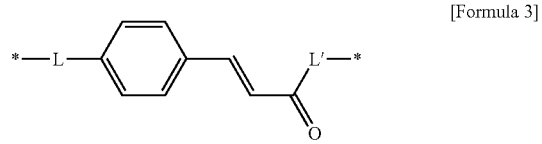

[Formula 3]

(wherein L and L' are respectively a nitrogen atom or an oxygen atom), $Y_1$ and $Y_2$ are the same as each other or different from each other, and respectively a direct bond or $C_{1-9}$ alkylene, X is selected from functional groups represented by Formulae 5 to 17:

[Formula 5]

wherein n is an integer ranging from 1 to 6,

[Formula 6]

wherein n is an integer ranging from 1 to 6,

[Formula 7]

[Formula 8]

-continued

[Formula 9]

[structure: triazine ring with three * substituents]

[Formula 10]

[structure: para-phenylene]

[Formula 11]

[structure: terephthaloyl]

[Formula 12]

[structure: biphenyl]

[Formula 13]

[structure: 4,4'-oxybis(phenoxy)]

[Formula 14]

[structure: diphenyl ether]

[Formula 15]

[structure: 4,4'-(phenyleneoxy)bis(phenoxy)]

[Formula 16]

[structure: diphenylmethane]

[Formula 17]

[structure: complex polyalkylated tri-aryl methane structure with CH$_3$ and C(CH$_3$)$_3$ substituents], and a is an integer ranging from 2 to 4.

2. The multi-functional monomer according to claim 1, wherein $Y_1$ and $Y_2$ of Formula 1 are respectively selected from functional groups represented by Formula 4:

[Formula 4]

$$*-(CH_2)_p-*$$

wherein p is an integer ranging from 0 to 9.

3. The multi-functional monomer according to claim 1, wherein the compound of Formula 1 is a compound of Formula 18:

[Formula 18]

[structure: symmetric compound with methacrylate-ethyleneoxy-cinnamoyl-phenoxy-terephthaloyl-phenoxy-cinnamoyl-ethyleneoxy-methacrylate]

4. The multi-functional monomer according to claim 1, wherein the compound of Formula 1 is a compound of Formula 19:

[Formula 19]

[structure: symmetric compound with methacrylate-ethyleneoxy-cinnamoyl-phenoxy-(C=O)-(CH$_2$)$_n$-(C=O)-phenoxy-cinnamoyl-ethyleneoxy-methacrylate]

wherein n is an integer ranging from 0 to 9.

5. The multi-functional monomer according to claim 1, wherein the compound of Formula 1 is a compound of Formula 20:

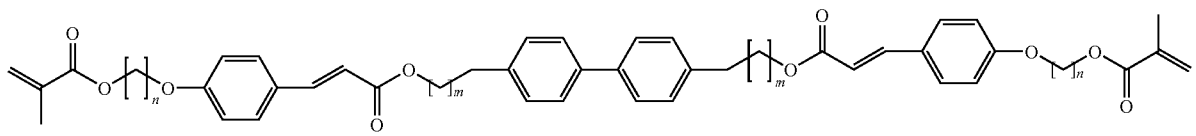

[Formula 20]

wherein m and n are respectively an integer ranging from 0 to 9.

6. The multi-functional monomer according to claim 1, wherein the compound of Formula 1 is a compound of Formula 21:

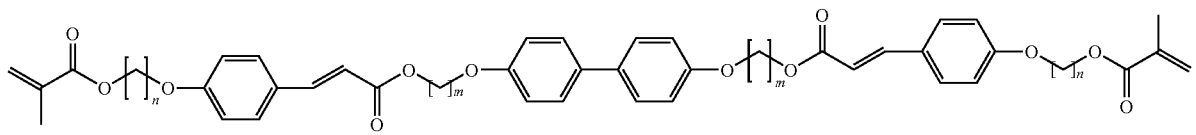

[Formula 21]

wherein m and n are respectively an integer ranging from 0 to 9.

7. The multi-functional monomer according to claim 1, wherein the compound of Formula 1 is a compound of Formula 22:

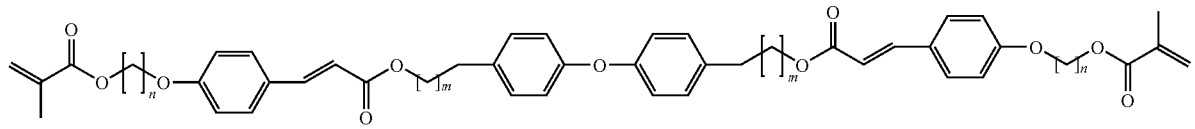

[Formula 22]

wherein m and n are respectively an integer ranging from 0 to 9.

8. The multi-functional monomer according to claim 1, wherein the compound of Formula 1 is a compound of Formula 23:

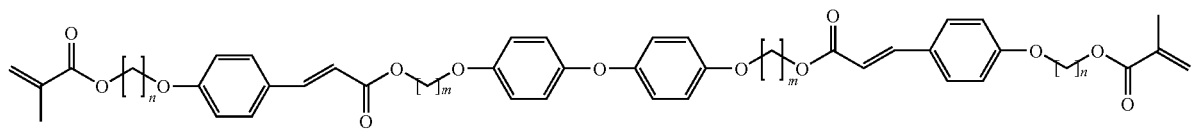

[Formula 23]

wherein m and n are respectively an integer ranging from 0 to 9.

9. The multi-functional monomer according to claim 1, wherein the compound of Formula 1 is a compound of Formula 24:

[Formula 24]

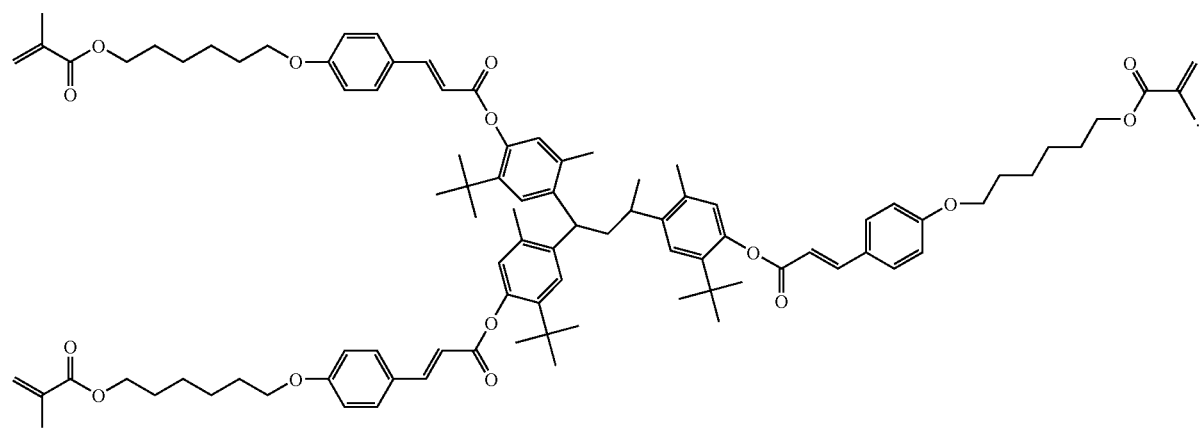

10. An alignment film for a liquid crystal display formed using the multi-functional monomer of claim 1.

11. The alignment film for a liquid crystal display according to claim 10, wherein the alignment film is produced using a method that comprises applying a solution, in which the multi-functional monomer is dissolved, on a substrate, removing a solvent from the applied solution to form a film, radiating polarized UV to provide anisotropy to a surface of the film, and heat treating the film to form a polymer film.

12. The alignment film for a liquid crystal display according to claim 11, wherein the alignment film is produced using the method that further comprises adding a photoinitiator to the solution in which the multi-functional monomer is dissolved, and performing photocuring at the same time the polarized UV is radiated or after the polarized UV is radiated.

13. The alignment film for a liquid crystal display according to claim 10, wherein the alignment film is 100 to 2,000 nm in thickness.

14. A liquid crystal display including the alignment film for the liquid crystal display of claim 10.

15. A method of producing an alignment film for a liquid crystal display, comprising:
 applying a solution in which the multi-functional monomer of claim 1 is dissolved on a substrate;
 removing a solvent from the applied solution to form a film;
 radiating polarized UV to provide anisotropy to a surface of the film; and
 heat treating the film to form a polymer film.

16. The method according to claim 15, further comprising:
 adding a photoinitiator to the solution in which the multi-functional monomer is dissolved; and
 performing photocuring at the same time the polarized UV is radiated or after the polarized UV is radiated.

* * * * *